United States Patent
Cummins et al.

(10) Patent No.: US 7,111,768 B2
(45) Date of Patent: Sep. 26, 2006

(54) SURGICAL STAPLING DEVICE

(76) Inventors: Christy Cummins, 9 Furnes Manor, Johnstown, Naas, County Kildare (IE); Paul Hooi, 105 Broadford Hill, Ballinteer, Dublin 16 (IE)

(*) Notice: Subject to any disclaimer, the term of this patent is extended or adjusted under 35 U.S.C. 154(b) by 0 days.

(21) Appl. No.: 10/519,778

(22) PCT Filed: Jul. 1, 2003

(86) PCT No.: PCT/IE03/00100

§ 371 (c)(1),
(2), (4) Date: Dec. 29, 2004

(87) PCT Pub. No.: WO2004/004578

PCT Pub. Date: Jan. 15, 2004

(65) Prior Publication Data

US 2005/0256537 A1    Nov. 17, 2005

(30) Foreign Application Priority Data

Jul. 3, 2002   (IE) ............................... S2002/0552

(51) Int. Cl.
*A61B 17/068* (2006.01)
*A61B 17/064* (2006.01)

(52) U.S. Cl. .................... 227/175.1; 227/19; 606/219; 606/151

(58) Field of Classification Search ............... 227/19, 227/175.1; 606/139, 142, 216, 219, 75, 151, 606/220, 221; 411/457–460, 473, 476, 920, 411/921

See application file for complete search history.

(56) References Cited

U.S. PATENT DOCUMENTS

| | | | |
|---|---|---|---|
| 3,482,428 A | 12/1969 | Kapitanov et al. | |
| 4,014,492 A | 3/1977 | Rothfuss | |
| 4,523,695 A | 6/1985 | Braun et al. | |
| 4,724,840 A | 2/1988 | McVay et al. | |
| 4,771,782 A | 9/1988 | Millar | |
| 4,789,090 A | 12/1988 | Blake, III | |
| 4,934,364 A | 6/1990 | Green | |
| 5,108,421 A | 4/1992 | Fowler | |
| 5,114,065 A * | 5/1992 | Storace ................... 227/175.1 | |
| 5,131,379 A | 7/1992 | Sewell, Jr. | |

(Continued)

FOREIGN PATENT DOCUMENTS

EP    0386361    9/1990

(Continued)

*Primary Examiner*—Scott A. Smith
*Assistant Examiner*—Gloria R. Weeks
(74) *Attorney, Agent, or Firm*—Nutter, McClennen & Fish LLP

(57) ABSTRACT

A surgical stapler comprises an elongate housing 10 and a surgical staple 14 slidable longitudinally within the housing towards the free forward end thereof. The back 18 of the staple has a rearward extension 22. An actuator 16 is slidable forwardly within the housing for driving the staple towards the free end of the housing. An upstanding flange 30 on the extension 22 engages a stop 32 within the housing to restrain the back of the staple against forward movement of the actuator bends the staple to bring the free ends of the legs towards one another to close the staple. Further movement of the actuator then ruptures the join between the extension and the back of the staple to release the closed staple.

16 Claims, 5 Drawing Sheets

U.S. PATENT DOCUMENTS

| | | | |
|---|---|---|---|
| 5,147,381 A | 9/1992 | Heimerl et al. | |
| 5,192,300 A | 3/1993 | Fowler | |
| 5,275,616 A | 1/1994 | Fowler | |
| 5,292,309 A | 3/1994 | Van Tassel et al. | |
| 5,306,254 A | 4/1994 | Nash et al. | |
| 5,395,030 A | 3/1995 | Kuramoto et al. | |
| 5,416,584 A * | 5/1995 | Kay | 356/475 |
| 5,431,639 A | 7/1995 | Shaw | |
| 5,443,481 A | 8/1995 | Lee | |
| 5,470,010 A | 11/1995 | Rothfuss et al. | |
| 5,478,352 A | 12/1995 | Fowler | |
| 5,527,322 A | 6/1996 | Klein et al. | |
| 5,536,251 A | 7/1996 | Evard et al. | |
| 5,544,802 A * | 8/1996 | Crainich | 227/176.1 |
| 5,560,532 A | 10/1996 | DeFonzo et al. | |
| 5,591,205 A | 1/1997 | Fowler | |
| 5,601,602 A | 2/1997 | Fowler | |
| 5,620,461 A | 4/1997 | Muijs Van De Moer et al. | |
| 5,643,318 A | 7/1997 | Tsukernik et al. | |
| 5,645,566 A | 7/1997 | Brenneman et al. | |
| 5,645,567 A * | 7/1997 | Crainich | 606/219 |
| 5,674,231 A | 10/1997 | Green et al. | |
| 5,676,689 A | 10/1997 | Kensey et al. | |
| 5,716,375 A | 2/1998 | Fowler | |
| 5,810,846 A | 9/1998 | Virnich et al. | |
| 5,855,312 A | 1/1999 | Toledano | |
| 5,861,005 A | 1/1999 | Kontos | |
| 5,902,310 A * | 5/1999 | Foerster et al. | 606/142 |
| 6,004,341 A | 12/1999 | Zhu et al. | |
| 6,007,563 A | 12/1999 | Nash et al. | |
| 6,022,372 A | 2/2000 | Kontos | |
| 6,048,358 A | 4/2000 | Barak | |
| 6,056,768 A | 5/2000 | Cates et al. | |
| 6,090,130 A | 7/2000 | Nash et al. | |
| 6,197,042 B1 | 3/2001 | Ginn et al. | |
| 6,277,140 B1 | 8/2001 | Ginn et al. | |
| 6,322,580 B1 | 11/2001 | Kanner | |
| 6,348,064 B1 | 2/2002 | Kanner | |
| 6,450,391 B1 * | 9/2002 | Kayan et al. | 227/176.1 |
| 6,506,210 B1 | 1/2003 | Kanner | |
| 6,533,762 B1 | 3/2003 | Kanner et al. | |
| 6,623,510 B1 | 9/2003 | Belef et al. | |
| 6,652,538 B1 * | 11/2003 | Kayan et al. | 606/143 |
| 6,719,777 B1 | 4/2004 | Ginn et al. | |
| 6,755,842 B1 | 6/2004 | Kanner et al. | |
| 6,767,356 B1 | 7/2004 | Kanner et al. | |
| 2002/0049472 A1 | 4/2002 | Coleman | |
| 2002/0151921 A1 | 10/2002 | Kanner et al. | |
| 2003/0097140 A1 | 5/2003 | Kanner | |
| 2003/0109890 A1 | 6/2003 | Kanner et al. | |
| 2004/0010285 A1 | 1/2004 | Carley et al. | |
| 2004/0254591 A1 | 12/2004 | Kanner et al. | |
| 2004/0267312 A1 | 12/2004 | Kanner et al. | |

FOREIGN PATENT DOCUMENTS

| | | |
|---|---|---|
| EP | 0 534 696 | 3/1993 |
| EP | 0756851 | 2/1997 |
| EP | 0774237 | 5/1997 |
| EP | 0941697 | 9/1999 |
| FR | 2443238 | 7/1980 |
| GB | 1358466 | 7/1974 |
| WO | WO-97/20505 | 6/1997 |
| WO | WO-98/17179 | 4/1998 |
| WO | WO-98/25508 | 6/1998 |
| WO | WO-00/56227 | 9/2000 |

\* cited by examiner

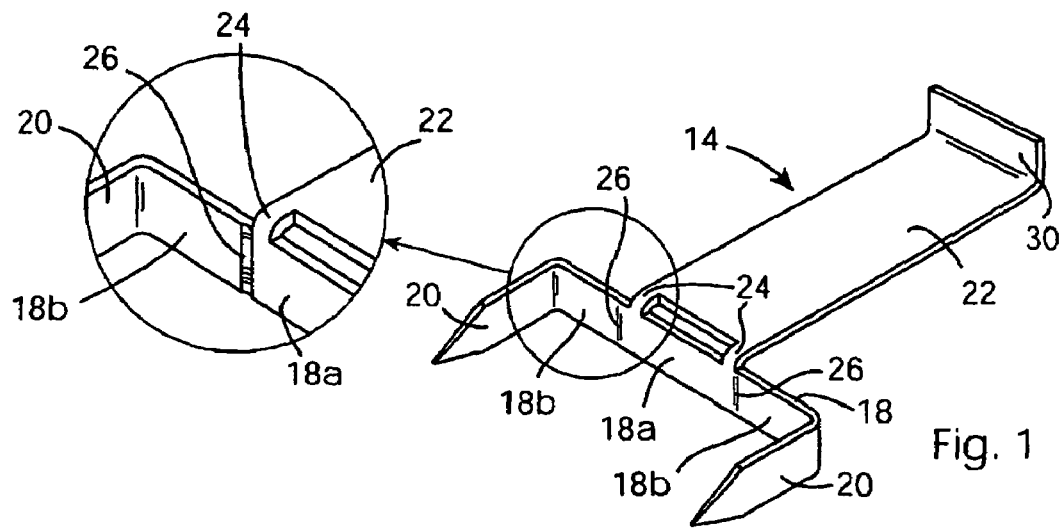
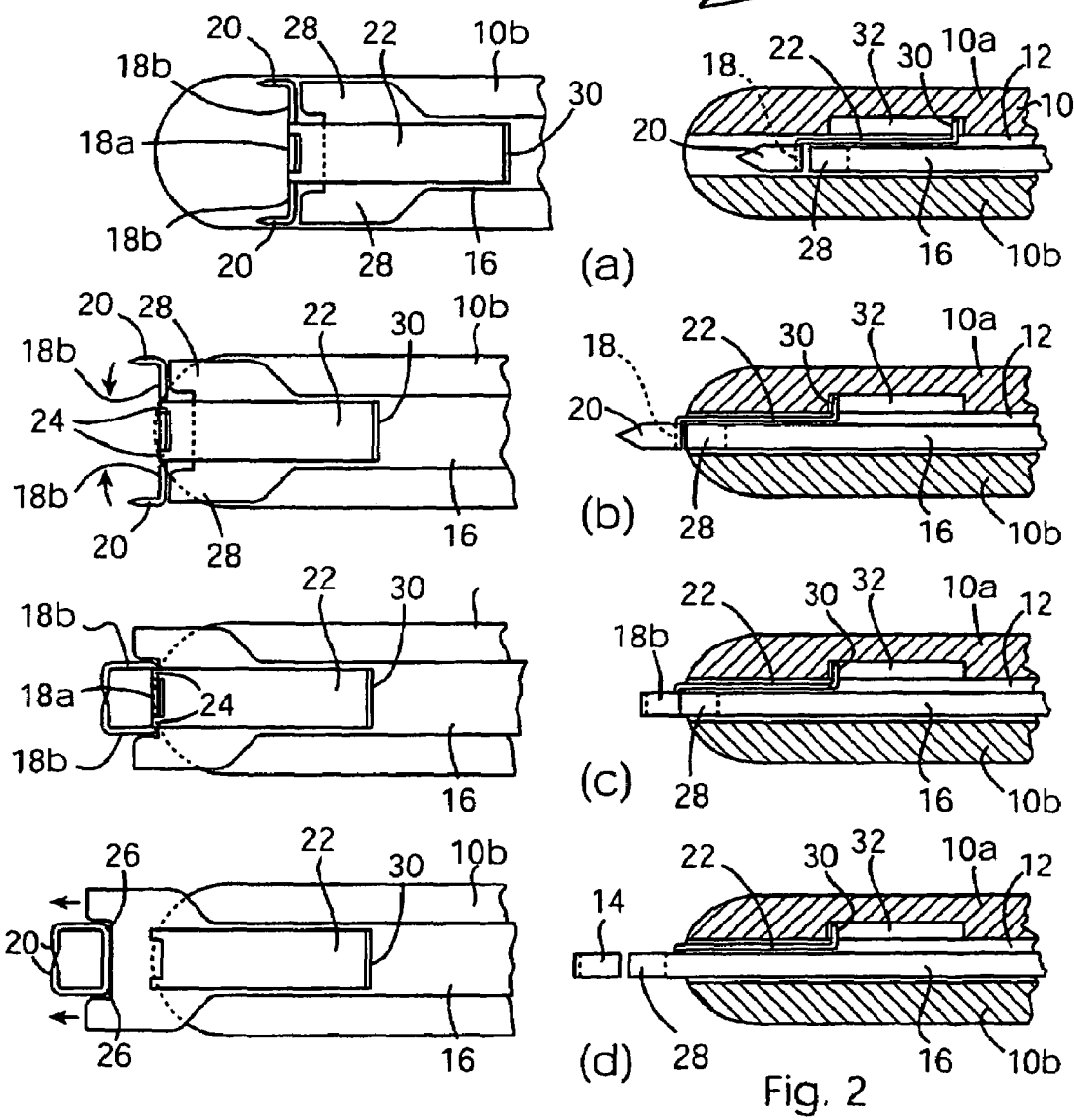
Fig. 1
Fig. 2

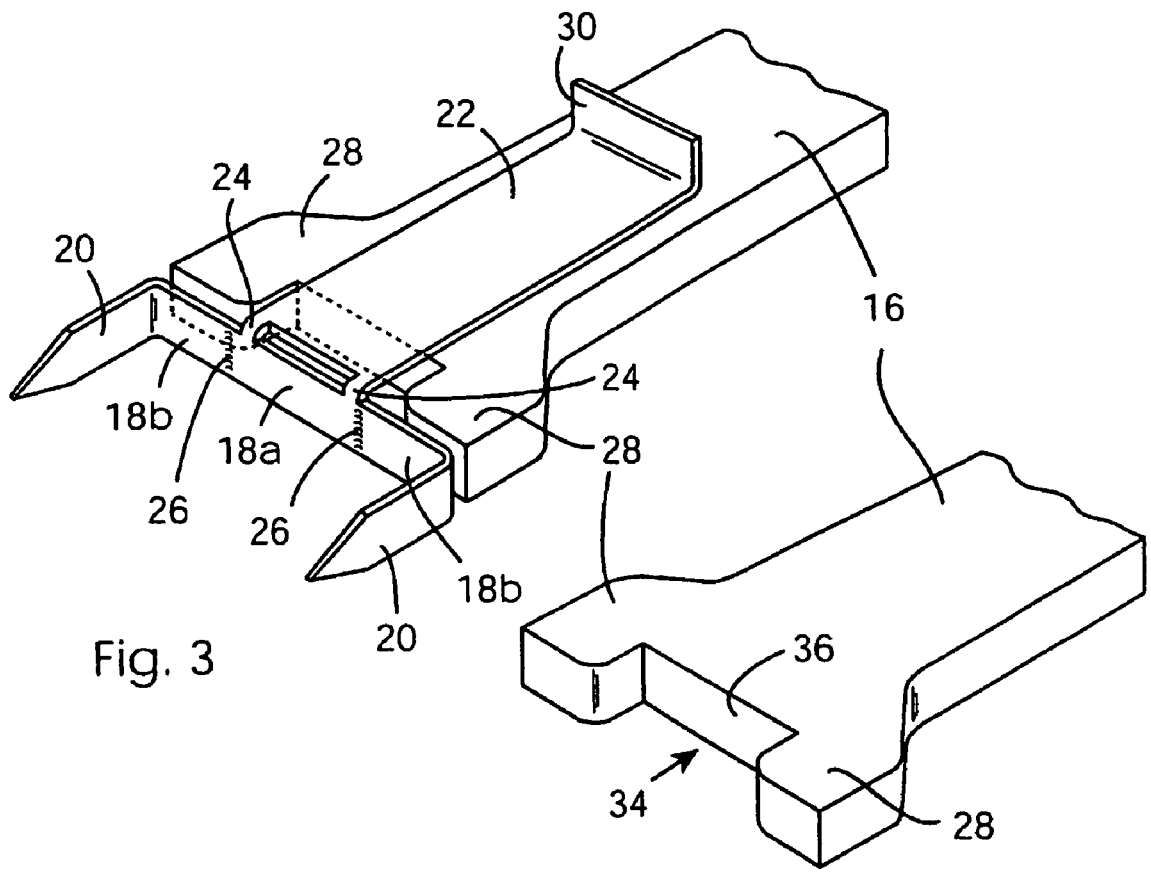
Fig. 3
Fig. 4
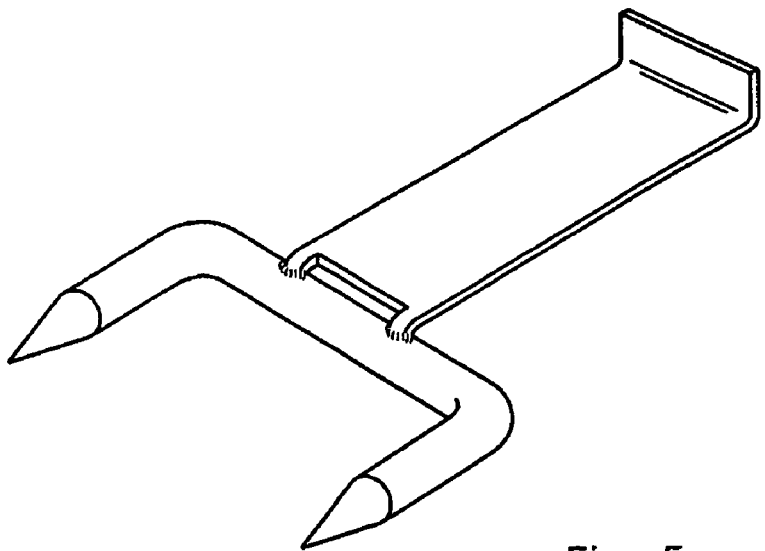
Fig. 5

SURGICAL STAPLING DEVICE

FIELD OF THE INVENTION

This invention relates to a surgical stapling device.

BACKGROUND

Surgical stapling devices have been in existence for many years. They are routinely used in surgical procedures mainly for the purposes of effecting a wound closure. Some of the most popular applications include closing a skin incision end-to-end or end-to-side anastomosis of internal (generally tubular) vessels such as the large bowel, etc. Current staplers are designed to deliver one or more staples in a serial fashion or a number of staples in one shot. Skin staplers, for example, deliver 30 or more staplers in a serial fashion. The staples are stacked within the device and during the firing operation one staple is advanced from the stack and delivered through the head of the device. During the following cycle another staple is advanced from the top of the stack and again delivered through the head of the device and so on. In one shot devices such as a bowel anastomosis stapler the staples are prearranged in a linear or circular fashion and upon activation of the device all the staples are delivered through the head. Examples of existing prior art as described above include U.S. Pat. Nos. 4,592,498, 5,289,963, 5,433,721 and 5,470,010.

The mechanism involved in forming a staple and releasing it from its forming mechanism is common to the majority of surgical stapler devices. Generally the components include an anvil, a staple closing actuator, and a staple release mechanism. The anvil is normally positioned in front of the staple and the actuator directly behind the staple. As the actuator advances the staple against the anvil the back section of the staple deforms around both ends of the anvil thereby transforming the staple from a generally U-shape to a generally rectangular shape. At this point the actuator generally retracts and the staple is released from the anvil either as a result of the anvil moving out of position and allowing the staple to move forward, or alternatively ejecting the staple over the anvil thereby releasing it from the device.

There are a number of problems associated with the mechanism as described above. Firstly, as the anvil is normally positioned in front of the staple it naturally becomes trapped between the back of the staple and the tissue into which it is being delivered causing the staple back to be spaced away from the tissue as opposed to lying tightly on its surface. This is a particular problem in the field of vascular puncture closure when it is desirable to keep the legs of the staple as short as possible so as to avoid having the legs of the staple within the vessel lumen.

Secondly, the method of releasing the staple from the anvil can be both complicated and unreliable. Metal springs are normally used which eject the staple over the anvil thereby affecting its release. However, should the spring fail to operate or is prohibited from operating properly by virtue of some tissue blockage etc, the device will become trapped in-situ.

Alternative release mechanisms include mechanical means of moving the anvil so that it is no longer in the path of the staple as it releases from the device. Again this generally involves very small metal components with relatively small movements which can fail to operate thereby leaving the staple trapped within the device and attached to the tissue into which it has been delivered.

Therefore there is a need for an improved surgical stapling device which will facilitate closer approximation of the staple back onto the surface of the vessel into which the staple is being delivered and a method of deforming the staple which does not include the use of an anvil component and therefore will not require the use of other components or mechanisms to facilitate the release of the staple from the anvil.

SUMMARY OF THE INVENTION

According to the present invention there is provided a surgical stapling device comprising an elongate housing, a surgical staple slidable longitudinally within the housing towards a free forward end thereof, the staple having a back and two forwardly pointing legs, an actuator slidable forwardly within the housing for driving the staple towards the free end of the housing, means for restraining the back of the staple against forward movement beyond a predetermined point such that further forward movement of the actuator bends the staple to bring the free ends of the legs towards one another to close the staple, and means for releasing the closed staple, wherein the back of the staple has a rearward extension and the restraining means comprises means for restraining the extension.

In a preferred embodiment the rearward extension is rupturably joined to the back of the staple, the staple being released by forward movement of the actuator beyond the point at which the staple is closed while the extension is restrained, thereby to rupture the join.

In another preferred embodiment a rearward extension is created which is integral to the staple back. This rearward extension creates a slot into which one end of an extension component is connected. Once the former has formed the staple around the anvil the extension is released from the staple during rearward movement of the former.

The benefits of the invention over conventional stapling devices is that, firstly, as no anvil is required the staple can be advanced forward to a position where the staple back is in direct contact with the tissue being stapled. This is of particular advantage when the staple legs must remain short but the level of penetration into the tissue must be assured. Secondly, because there is no anvil component involved in the delivery mechanism, there is no requirement to add additional components so as to facilitate ejection of the staple over or around the anvil component or alternatively to move the anvil component to a position which allows the staple to advance forward and free up the device.

BRIEF DESCRIPTION OF THE DRAWINGS

Embodiments of the invention will now be described, by way of example, with reference to the accompanying drawings, in which:

FIG. 1 is a perspective view of a staple with a restraining plate for use in an embodiment of the invention;

FIGS. 2(a) to 2(d) are plan views (left hand column) and equivalent sectional views (right hand column) of a stapling device according to the embodiment in successive stages of operation;

FIG. 3 is a perspective view of the staple and actuator assembly of FIG. 2;

FIG. 4 is a perspective view of the forward tip of the actuator of FIG. 2; and

FIGS. 5 to 12 are perspective view of further embodiments of staple for use with a device according to the invention.

DETAILED DESCRIPTION OF THE INVENTION

Figure 6:
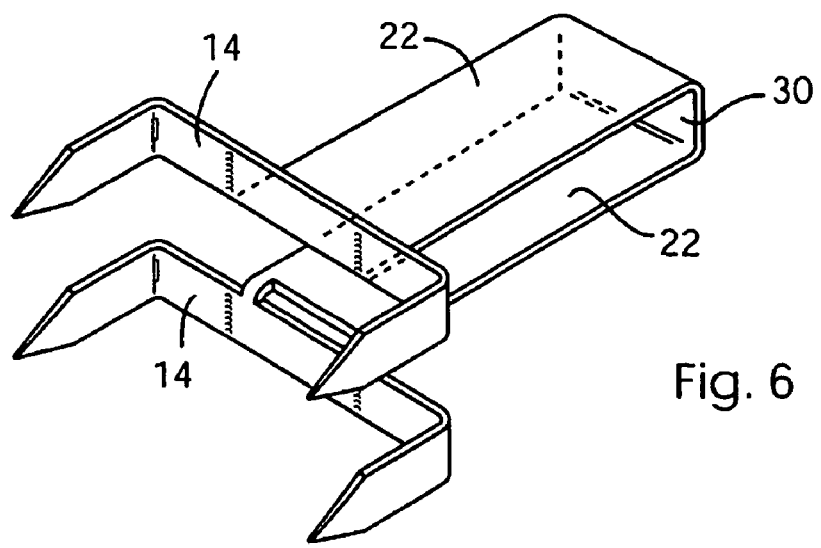

In the drawings the same reference numerals have been used for the same or equivalent parts.

Referring to FIGS. 1 to 4, a surgical stapling device comprises an elongated housing or shaft 10 having upper and lower halves 10a and 10b defining between them a longitudinal channel 12 for slidably accommodating a staple 14 and a staple closing actuator 16 (in the plan views in the left hand column of FIG. 2 only the lower housing half 10b is shown). Only the free forward end of the housing 10 is shown in the drawings, since that is where the invention lies in the present embodiment. The rear end of the housing 10 is preferably formed with a pistol grip and the movement of the various components to be described may be effected by a trigger acting through a cam system. Such an arrangement is described in Irish Patent Application S2000/0722 which may be readily adapted to operate the device of the present embodiment.

The staple 14 is generally U-shaped, having a back 18 and two forwardly pointing legs 20. The free ends of the staple legs 20 are sharpened for ease of tissue penetration. Integral with the staple back 18 there is a rearwardly extending plate 22 which is attached to the upper edge of the centre section 18a of the staple back by a pair of narrow, relatively weak tabs 24. The tabs are effectively thin metal bridges which connect the staple back to the plate 22. At the rear end of the plate 22 there is an upstanding flange 30 perpendicular to the plane of the plate 22. In this embodiment the staple 14 including the plate 22 and flange 30 is made as an integral structure from stamped and bent sheet metal stock, for example, a malleable metal or metal alloy such as stainless steel or titanium.

Adjacent to the tabs 24, at the junctions 26 between the centre section 18a and the outer sections 18b of the staple back on either side, and where in use the staple back is designed to bend through an angle of 90° as will be described, local deformation of the material of the staple is provided so as to ensure that bending takes place preferentially at those points.

The actuator 16 is an elongated rod having a forward end which is forked to provide two arms 28 separated by a recess 34. The lateral separation of the arms 28 is slightly greater than the distance between the junctions 26 on the back 18 of the staple.

The device is assembled (FIG. 2) with the actuator 16 extending longitudinally in the channel 12 with its forked end facing towards the free forward end of the housing 10. The staple 14 is positioned freely in front of the actuator 16 with its back 18 transverse to the axis of the housing 10 with the plate 22 extending rearwardly across the top surface of the actuator. The flange 30 extends up into a recess 32 in the top housing half 10a. The actuator arms 28 are behind and in alignment with the outer sections 18b of the staple back.

In use, both the staple 14 and the actuator 16 are initially retracted, FIG. 2(a), so that the flange 30 is adjacent the rear end of the recess 32 and the entire staple 14 is contained wholly within the housing 10. Upon operation of the trigger previously mentioned, or other operating mechanism, the actuator 16 is driven forwardly towards the free forward end of the housing 10. This drives the staple 14 before it by engagement of the actuator arms 28 with the outer sections 18b of the staple back.

At a predetermined point, FIG. 2(b), where the back of the staple is substantially level with the forward end of the housing 10, the flange 30 comes up against the front end of the recess 32. The flange 30 and front end of the recess 32 act as cooperating stop means which, via the plate 22, restrain the centre section 18a of the staple back against further forward movement. Thus, as the actuator 16 continues to advance, the actuator arms 28 bend the outer sections 18b of the back of the staple forwardly through 90° to bring the free ends of the staple legs 20 towards one another and deform the staple into a generally rectangular closed shape, FIG. 2(c).

At this point the base 36 of the recess 34 in the front of the actuator 16 is abutting against the centre section 18a of the staple base. Now, since the plate 22 remains restrained by engagement of the stop means 30/32 further forward movement of the actuator 16 will rupture the tabs 24 thus freeing the staple from the plate 22. At this point the cycle is complete.

FIG. 5 shows an alternative embodiment for the staple. It comprises a standard round wire staple 40 having a rearwardly extending restraining plate 22 with upstanding flange 30 attached to the centre section of the staple back by rupturable tabs 24. The tabs may be attached to the staple back by soldering, braising, laser welding, adhesive bonding, etc. The preferred process will ensure a consistent break-off force between the tabs and the staple back.

Referring now to FIG. 6, another embodiment of the staple is shown which includes two staples 14 disposed spaced apart one above and each having a respective rearwardly-extending restraining plate 22 joined thereto by rupturable tabs as previously described. In this case the rear ends of the parallel plates are joined by a common flange 30. In such a case the stapling device would be modified such that stop means on the housing 10 projected into the space between the upper and lower plates 22 and engaged the flange 30 between them to restrain the back of the staple. The double staple could be driven by two actuators 16, one disposed above the upper plate 22 and the other below the lower plate 22, or a single actuator could be used having upper and lower branches which embrace the plates 22 between them.

Figure 7:
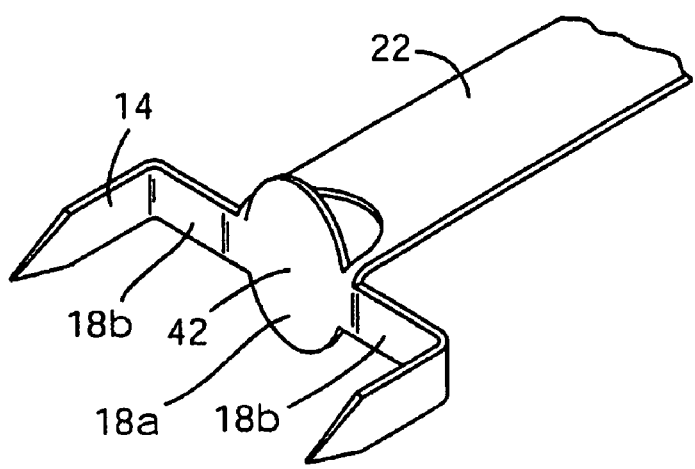

FIG. 7 shows another staple usable in the invention in which the centre section 18a of the staple back is enlarged, for example by forming it as a disk 42, so that the centre section 18a has a much greater area in a plane normal to the longitudinal axis of the housing 10 than either of the outer section 18b. This configuration has particular application in the field of vascular puncture closure. The process of closing puncture holes using conventional staples may be enhanced using this method as the disk 42 on the staple back provides greater surface coverage of the puncture hole area thereby effecting haemostasis in a shorter time.

Figure 8:
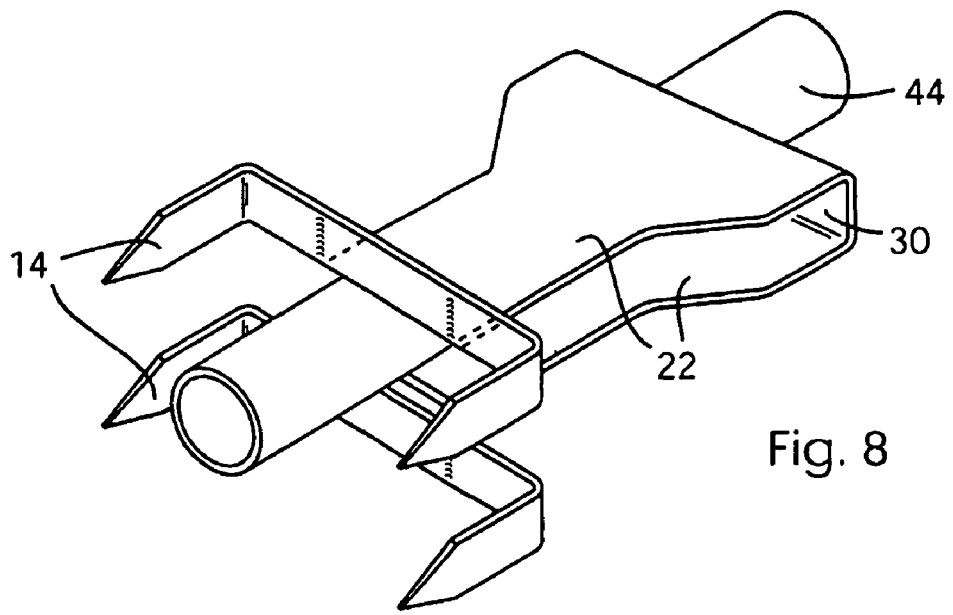

FIG. 8 shows a configuration which is essentially the double staple as described in FIG. 6 but for use in combination with a stapling device having a locator tube 44. The locator tube 44, which passes between the plates 22 through a hole (not shown) in the flange 30, is slidable axially within the housing 10 between a forward position wherein it projects beyond the free forward end of the housing 10 to enter a puncture site in a liquid-carrying vessel in a human or animal, thereby to locate the free end of the housing at the puncture site, and a rearward position wherein the locator tube is retracted into the housing. In use a guidewire (not shown) extends within the locator tube and emerges from the forward end of the tube, the tube 44 being tracked along the guidewire to the puncture site and the guidewire and tube being retracted into the housing prior to closure of the staples. A locator tube is described in the aforementioned Irish Patent Application S2000/0722, and it will be clear to one skilled in the art how to modify the embodiment shown in FIG. 2 to incorporate such a tube. This configuration has particular relevance in the area of vascular puncture closure.

The staple configurations shown in FIGS. 6 to 8 are, like the staple shown in FIG. 1, designed so that they are easily manufactured as integral structures from sheet metal using a conventional metal stamping and bending processes.

Figure 9:
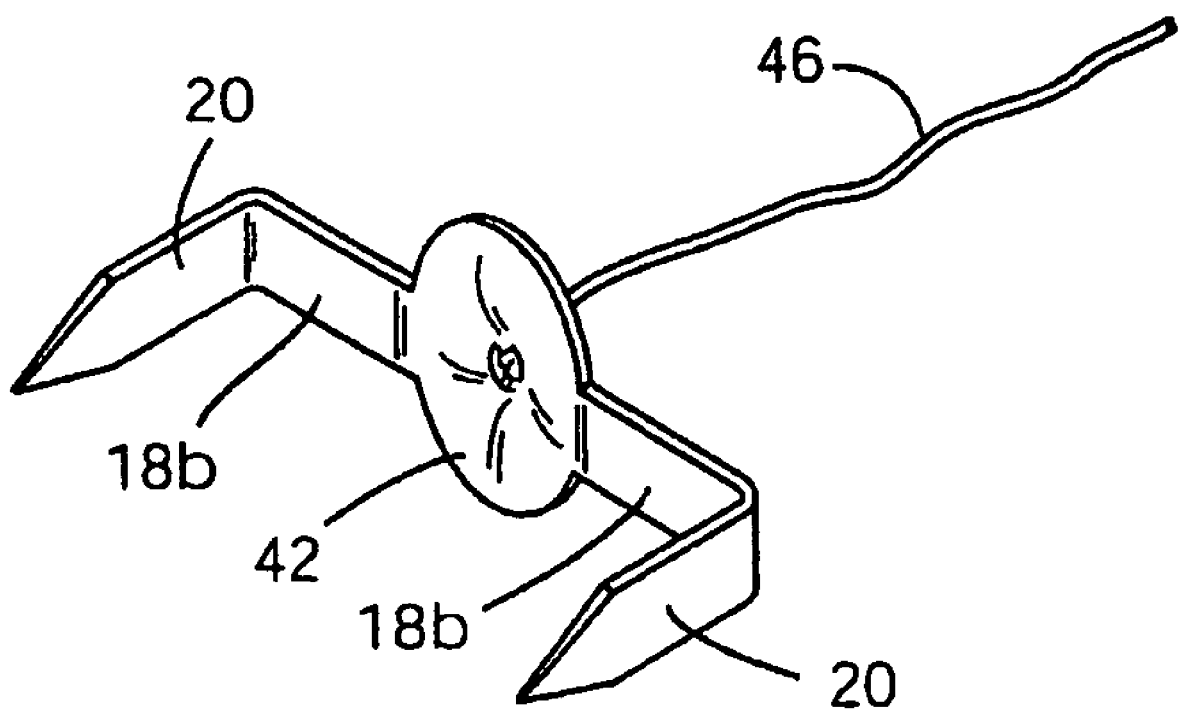

The embodiment of staple shown in FIG. 9 comprises a staple essentially as described with reference to FIG. 7 but without the attached plate 22. Instead, a rearwardly extending filament 46 is attached to the rear surface of the disk 42. In use, the stapling device is adapted to trap or hold the rear end of the filament 46 so that it becomes taut at the point where the staple back is level with the front end of the housing 10 so that further advance of the actuator will bend the outer sections 18b of the staple back to close the staple as previously described. At this point the actuator may advance further forward thereby shearing or detaching the filament from the back surface of the disk 42. Alternatively, the actuator may retract while simultaneously the device releases the filament at its rear end and consequently releasing the staple from the device. Examples of the filament material are Dacron, PLA, PGA and PLGA.

Figure 10:
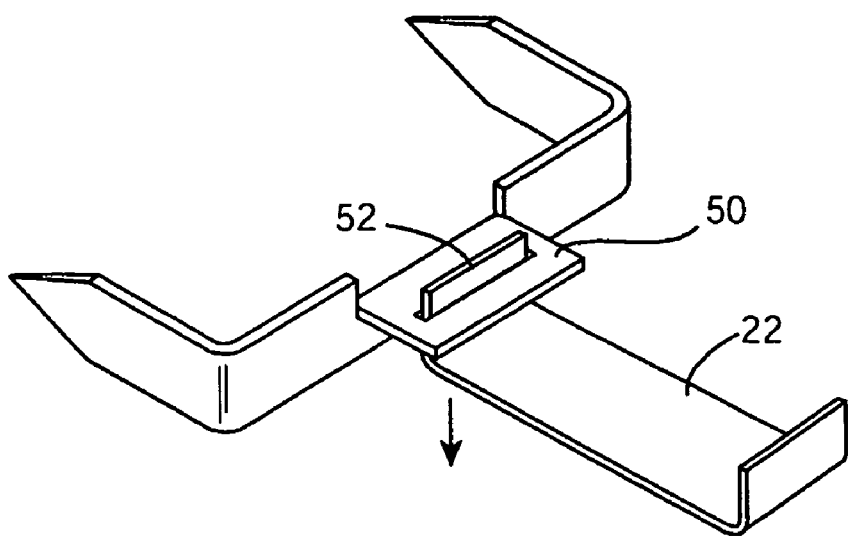

In FIG. 10 a staple configuration is shown similar to that in FIG. 3 except that the rupture tabs 24 are replaced with a slotted tab 50 which engages with an upstanding flange 52 integral to plate 22. As the former advances forward to form the staple the back is held in position by the plate 22. Once forming is complete the former component retracts while simultaneously causing the plate 22 to move down disengaging the flange 52 from the staple slot 50 allowing it to separate from the stapler device.

Figure 11:
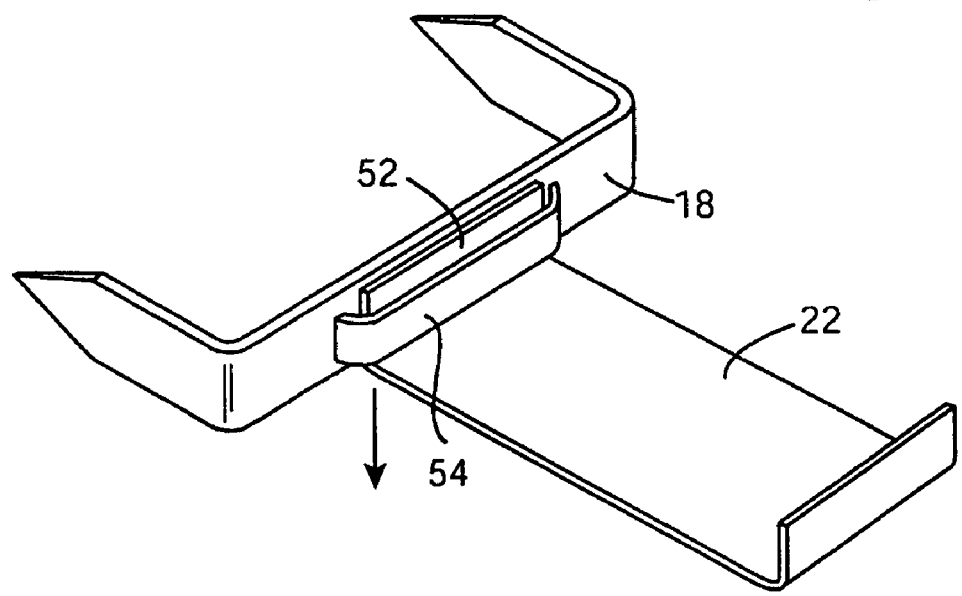
Figure 12:
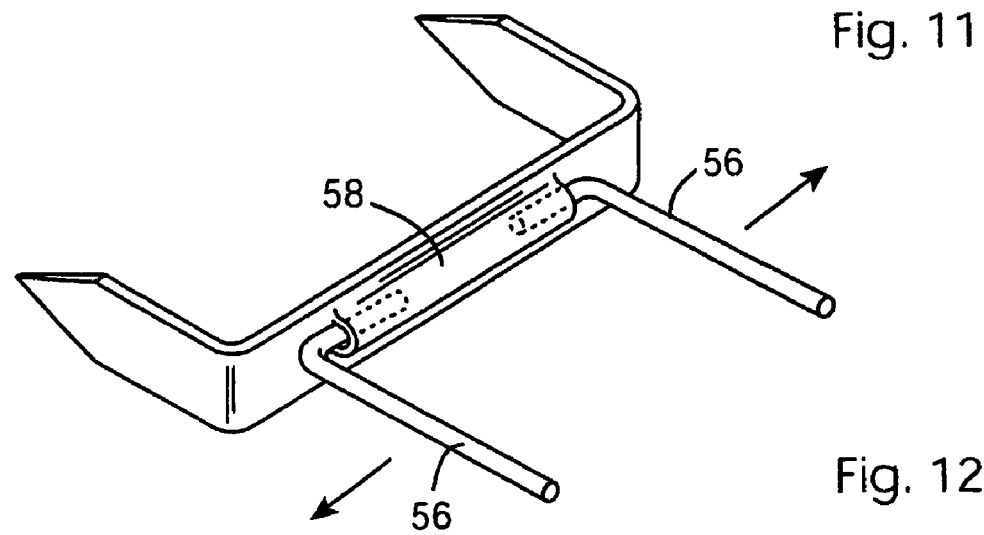

FIGS. 11 and 12 illustrate further embodiments of this principle. In FIG. 11 the flange 52 engages a band 54 which is formed integrally with an lies parallel to the back 18 of the staple. In FIG. 12 a pair of L-shaped cylindrical arms engage a channel section 58 of the staple back 18 to restrain the staple during forming. When forming is complete the former retracts while simultaneously causing the arms 56 to be pushed outwards, away from one another and out of engagement with the channel section 58.

The invention is not limited to the embodiments described herein and may be modified or varied without departing from the scope of the invention.

The invention claimed is:

1. A surgical stapling device, comprising:
   an elongate housing;
   a surgical staple slidable longitudinally within the housing towards a free forward end thereof, the staple having two forwardly pointing legs and a back having a rearward extension;
   an actuator slidable forwardly within the housing for driving the staple towards the free end of the housing;
   means for restraining the rearward extension on the back of the staple against forward movement beyond a predetermined point such that further forward movement of the actuator bends the staple to bring the free ends of the legs towards one another to close the staple; and
   means for releasing the closed staple.

2. The device of claim 1, wherein the rearward extension is rupturably joined to the back of the staple such that the staple is released by forward movement of the actuator beyond the predetermined point at which the staple is closed while the extension is restrained.

3. The device of claim 1, wherein the back of the staple is disposed substantially transverse the longitudinal axis of the housing and the two forwardly pointing legs extend at an angle from opposite ends of the back, the back of the staple having a center section and two outer sections, the actuator engaging the outer sections of the back of the staple and the restraining means restraining the center section of the staple back such that further forward movement of the actuator bends the outer sections of the back of the staple forwardly relative to the center section.

4. The device of claim 3, wherein the back of the staple is adapted for preferential bending at the junction between the center and outer sections.

5. The device of claim 3, wherein the center section of the back of the staple has a greater area in a plane normal to the longitudinal axis of the housing than the outer sections.

6. The device of claim 1, wherein the extension extends rigidly from the staple back and has a stop means which comes to abut against a cooperating stop means within the housing when the back of the staple reaches the predetermined point.

7. The device of claim 1, wherein there are two staples disposed spaced apart one above the other and each has a respective rearward extension, the rearward extensions being connected together and both staples being driven forwardly and closed simultaneously by at least one actuator.

8. The device of claim 7, further including an elongated locator member slidable axially within the housing between a forward position wherein the locator member projects beyond the free end of the housing to enter a puncture site in a liquid-carrying vessel in a human or animal, thereby to locate the free end of the housing at the puncture site, and a rearward position wherein the locator member is retracted into the housing, the locator member passing between the two rearward extensions and being retracted into the housing prior to closure of the staples.

9. The device of claim 8, wherein the locator member comprises a hollow tube and a guidewire extends within the locator tube and emerges from the forward end of the tube.

10. The device of claim 1, wherein the staple and rearward extension are made as an integral structure by stamping and bending a metal sheet.

11. A surgical stapling device, comprising:
    an elongate housing adapted to slidably receive a surgical staple and to drive a staple forwardly to a predetermined position at which an extension on the staple is effective to restrain the staple to the predetermined position and further forward movement of the staple is effective to bend at least one leg on the staple and to release the staple from the extension.

12. The device of claim 11, further comprising an actuator slidable longitudinally within the housing for driving the staple forwardly.

13. The device of claim 11, wherein the extension is rupturably joined to the staple.

14. A method for closing a puncture wound in tissue, comprising:
    positioning a forward end of an elongate housing adjacent to a puncture wound in tissue;
    advancing an actuator forwardly through the elongate housing to advance a staple to a predetermined position, the staple having a restraining means for restraining the staple against further forward movement;
    further advancing the actuator forwardly to move at least one leg on the staple to close the staple, and to release the staple from the restraining means.

15. The method of claim 14, wherein the at least one leg of the staple extends through the tissue adjacent the puncture wound and a back of the staple is positioned in direct contact with the tissue when the staple is in the predetermined position.

16. The method of claim 14, wherein the restraining means comprises an extension extending from a back of the staple, the extension being rupturably joined to the back of the staple to release the staple therefrom.

* * * * *